US008725536B2

(12) United States Patent
Deobhakta et al.

(10) Patent No.: US 8,725,536 B2
(45) Date of Patent: May 13, 2014

(54) ESTABLISHING A PATIENT-PROVIDER CONSENT RELATIONSHIP FOR DATA SHARING

(75) Inventors: Kalpita Deobhakta, Redmond, WA (US); Sean Nolan, Bellevue, WA (US); Hubert Van Hoof, Seattle, WA (US)

(73) Assignee: Microsoft Corporation, Redmond, WA (US)

( * ) Notice: Subject to any disclaimer, the term of this patent is extended or adjusted under 35 U.S.C. 154(b) by 1441 days.

(21) Appl. No.: 12/163,310

(22) Filed: Jun. 27, 2008

(65) Prior Publication Data

US 2009/0326982 A1    Dec. 31, 2009

(51) Int. Cl.
G06F 21/30 (2013.01)
G06F 21/31 (2013.01)
H04L 9/00 (2006.01)
H04L 9/32 (2006.01)

(52) U.S. Cl.
USPC ............... 705/3; 705/2; 713/182; 713/193

(58) Field of Classification Search
USPC ........................................... 705/2–3
See application file for complete search history.

(56) References Cited

U.S. PATENT DOCUMENTS

| | | | |
|---|---|---|---|
| 6,101,478 A | 8/2000 | Brown | |
| 6,757,898 B1 | 6/2004 | Ilsen et al. | |
| 6,850,889 B1 | 2/2005 | Zayas | |
| 7,020,618 B1 | 3/2006 | Ward | |
| 7,275,220 B2 | 9/2007 | Brummel et al. | |
| 2001/0054155 A1* | 12/2001 | Hagan et al. ............... | 713/193 |
| 2003/0088441 A1 | 5/2003 | McNerney | |
| 2003/0225597 A1 | 12/2003 | Levine | |
| 2004/0172307 A1 | 9/2004 | Gruber | |
| 2004/0225528 A1 | 11/2004 | Brock | |
| 2005/0010780 A1* | 1/2005 | Kane et al. ............... | 713/182 |
| 2005/0192845 A1 | 9/2005 | Brinsfield et al. | |
| 2006/0004588 A1* | 1/2006 | Ananda ............... | 705/1 |
| 2006/0155668 A1 | 7/2006 | Miller et al. | |
| 2006/0229918 A1* | 10/2006 | Fotsch et al. ............... | 705/3 |
| 2007/0016450 A1 | 1/2007 | Bhora et al. | |
| 2007/0192140 A1 | 8/2007 | Gropper | |
| 2007/0282637 A1 | 12/2007 | Smith | |
| 2008/0046292 A1 | 2/2008 | Myers et al. | |

FOREIGN PATENT DOCUMENTS

WO    WO2006091956 A2    8/2006

OTHER PUBLICATIONS

Bank of Queensland Enhanced Internet Banking, Nov. 2006 (from www.archive.org), www.boq.com.au/online_enhancedIB_security_token.htm.*
Bank of Queensland Enhanced Internet Banking, Nov. 2006 (from www.archive.org), www.boq.com.au/online_enhancedICB_security_token.htm.*

(Continued)

Primary Examiner — Joy Chng
(74) Attorney, Agent, or Firm — Damon Rieth; Jim Ross; Micky Minhas

(57) ABSTRACT

A shared secret may be shared between a patient and the patient's healthcare provider. The healthcare provider may submit the shared secret to the database system via a provider interface to generate a validation code. The validation code may be later submitted to the database system by the patient via a patient interface to cause the database system to prompt the patient to submit the shared secret. Upon submission of the shared secret to the database system, the patient may be prompted to approve or deny a request of the healthcare provider to access the electronic medical record of the patient. Access may be granted to the healthcare provider upon approval of the request by the patient.

20 Claims, 11 Drawing Sheets

(56) References Cited

OTHER PUBLICATIONS

"Microsoft HealthVault Beta: How HealthVault works", 2008, Microsoft, p. 1.

"MedInformatix Practice Management", 1999-2006, MedInformatix Inc., pp. 2.

Blankenhorn, "Microsoft Releases Hospital IT System as Amalga", Feb. 13, 2008, ZDNet Healthcare, pp. 2.

Mandl, et al., "HealthConnect: Clinical Grade Patient-Physician Communication", Proceedings of AMIA Symposium, 1999, pp. 5.

Santiago, "Privacy and Security Solutions for Interoperable Health Information Exchange", NC HISPC Interim Analysis of Solutions Report, Jan. 15, 2006, pp. 47.

"Privacy Policy", 2007, Empower Med, Inc., pp. 7.

"Google Health Unveils Electronic Record Pilot", Feb. 22, 2008, E-Health-Media, pp. 2.

"Privacy and Consent Agreements", retrieved at << hhpeds.com/files/Privacy_and_Consent_Agreements2.doc >>, pp. 2.

* cited by examiner

| CLINICAL SYSTEM | ELECTRONIC DATABASE SYSTEM |
|---|---|

MASTER_APPLICATION_ID
"123ID"

CHILD_APPLICATON_ID "ABCID"
FOR PROVIDER_IDENTIFIER
"ABC CLINIC"

PATIENTS

| PATIENT_ID | AAA |
|---|---|
| PERSON_ID | NULL |
| RECORD_ID | NULL |
| ...MORE INFO... | ... |

PENDING_REQUESTS

| VALIDATION_CODE | NULL |
|---|---|
| VALIDATION_QUESTION | NULL |
| VALIDATION_ANSWER | NULL |
| CHILD_APPLICATION_ID | NULL |
| PATIENT_ID | NULL |
| PERSON_ID | NULL |
| RECORD_ID | NULL |
| STATUS | NULL |

APPLICATIONS

| MASTER_APPLICATION_ID | 123ID |
|---|---|
| CHILD_APPLICATION_ID | ABCID |
| PUBLIC_KEY | ... |
| PROVIDER_ID | ABC CLINIC |
| REQUESTED_DATA | R/W MEDICATIONS |
| PRIVACY STATEMENT | LINK_1 |
| SERVICE_AGREEMENT | LINK_2 |
| ...MORE INFO... | ... |

APPLICATION_AUTHORIZATIONS

| CHILD_APPLICATION_ID | NULL |
|---|---|
| PERSON_ID | NULL |
| RECORD_ID | NULL |
| AUTHORIZATION_RULES | NULL |

FIG. 7

| CLINICAL SYSTEM | ELECTRONIC DATABASE SYSTEM |
|---|---|

CLINICAL SYSTEM

MASTER_APPLICATION_ID
"123ID"

CHILD_APPLICATON_ID "ABCID"
FOR PROVIDER_IDENTIFIER
"ABC CLINIC"

| PATIENTS ||
|---|---|
| PATIENT_ID | AAA |
| PERSON_ID | NULL |
| RECORD_ID | NULL |
| ...MORE INFO... | ... |

ELECTRONIC DATABASE SYSTEM

| PENDING_REQUESTS ||
|---|---|
| VALIDATION_CODE | ABCDEFG |
| VALIDATION_QUESTION | FIRST PET? |
| VALIDATION_ANSWER | SEEDS |
| CHILD_APPLICATION_ID | ABCID |
| PATIENT_ID | AAA |
| PERSON_ID | NULL |
| RECORD_ID | NULL |
| STATUS | PENDING |

| APPLICATIONS ||
|---|---|
| MASTER_APPLICATION_ID | 123ID |
| CHILD_APPLICATION_ID | ABCID |
| PUBLIC_KEY | ... |
| PROVIDER_ID | ABC CLINIC |
| REQUESTED_DATA | R/W MEDICATIONS |
| PRIVACY STATEMENT | LINK_1 |
| SERVICE_AGREEMENT | LINK_2 |
| ...MORE INFO... | ... |

| APPLICATION_AUTHORIZATIONS ||
|---|---|
| CHILD_APPLICATION_ID | NULL |
| PERSON_ID | NULL |
| RECORD_ID | NULL |
| AUTHORIZATION_RULES | NULL |

FIG. 8

| CLINICAL SYSTEM | ELECTRONIC DATABASE SYSTEM |
|---|---|

MASTER_APPLICATION_ID
"123ID"

CHILD_APPLICATON_ID "ABCID"
FOR PROVIDER_IDENTIFIER
"ABC CLINIC"

| PATIENTS | |
|---|---|
| PATIENT_ID | AAA |
| PERSON_ID | NULL |
| RECORD_ID | NULL |
| ...MORE INFO... | ... |

| PENDING_REQUESTS | |
|---|---|
| VALIDATION_CODE | ABCDEFG |
| VALIDATION_QUESTION | FIRST PET? |
| VALIDATION_ANSWER | SEEDS |
| CHILD_APPLICATION_ID | ABCID |
| PATIENT_ID | AAA |
| PERSON_ID | 111111 |
| RECORD_ID | 222222 |
| STATUS | ACCEPTED |

| APPLICATIONS | |
|---|---|
| MASTER_APPLICATION_ID | 123ID |
| CHILD_APPLICATION_ID | ABCID |
| PUBLIC_KEY | ... |
| PROVIDER_ID | ABC CLINIC |
| REQUESTED_DATA | R/W MEDICATIONS |
| PRIVACY STATEMENT | LINK_1 |
| SERVICE_AGREEMENT | LINK_2 |
| ...MORE INFO... | ... |

| APPLICATION_AUTHORIZATIONS | |
|---|---|
| CHILD_APPLICATION_ID | ABCID |
| PERSON_ID | 111111 |
| RECORD_ID | 222222 |
| AUTHORIZATION_RULES | R/W MEDICATIONS |

FIG. 9

| CLINICAL SYSTEM | ELECTRONIC DATABASE SYSTEM |
|---|---|

MASTER_APPLICATION_ID
"123ID"

CHILD_APPLICATON_ID "ABCID"
FOR PROVIDER_IDENTIFIER
"ABC CLINIC"

| PATIENTS | |
|---|---|
| PATIENT_ID | AAA |
| PERSON_ID | 111111 |
| RECORD_ID | 222222 |
| ...MORE INFO... | ... |

| PENDING_REQUESTS | |
|---|---|
| VALIDATION_CODE | ABCDEFG |
| VALIDATION_QUESTION | FIRST PET? |
| VALIDATION_ANSWER | SEEDS |
| CHILD_APPLICATION_ID | ABCID |
| PATIENT_ID | AAA |
| PERSON_ID | 111111 |
| RECORD_ID | 222222 |
| STATUS | COMPLETE |

| APPLICATIONS | |
|---|---|
| MASTER_APPLICATION_ID | 123ID |
| CHILD_APPLICATION_ID | ABCID |
| PUBLIC_KEY | ... |
| PROVIDER_ID | ABC CLINIC |
| REQUESTED_DATA | R/W MEDICATIONS |
| PRIVACY STATEMENT | LINK_1 |
| SERVICE_AGREEMENT | LINK_2 |
| ...MORE INFO... | ... |

| APPLICATION_AUTHORIZATIONS | |
|---|---|
| CHILD_APPLICATION_ID | ABCID |
| PERSON_ID | 111111 |
| RECORD_ID | 222222 |
| AUTHORIZATION_RULES | R/W MEDICATIONS |

FIG. 10

|  | ACTION IDENTIFIER | |
|---|---|---|
| MEDICAL INFORMATION | READ | WRITE |
| MEDICATIONS | APPROVED | APPROVED |
| ALLERGIES | DENIED | DENIED |
| IMMUNIZATIONS | APPROVED | DENIED |
| PERSONAL DEMOGRAPHICS | DENIED | APPROVED |
| CONDITIONS | NULL | NULL |
| ETC. | NULL | NULL |

FIG. 11

ESTABLISHING A PATIENT-PROVIDER CONSENT RELATIONSHIP FOR DATA SHARING

BACKGROUND

Electronic medical records (EMR) may be used by healthcare providers to conveniently store medical information of their patients. Electronic medical records may also enable healthcare providers to conveniently share medical information of their patients with other healthcare providers. A variety of privacy rules dictating how medical information may be shared by healthcare providers have been created to deal with a variety of issues relating to such electronic medical records. Some privacy rules do not permit a patient's electronic medical record to be shared with other healthcare providers without first obtaining consent from the patient.

SUMMARY

An approach for obtaining consent from a patient to access an electronic medical record of the patient stored at a database system is disclosed. As one example, a shared secret may be shared between a patient and the patient's healthcare provider. The healthcare provider may submit the shared secret to the database system via a provider interface to generate a validation code. The validation code may be later submitted to the database system by the patient via a patient interface to cause the database system to prompt the patient to submit the shared secret. Upon submission of the shared secret to the database system, the patient may be prompted to approve or deny a request of the healthcare provider to access the electronic medical record of the patient. Access may be granted to the healthcare provider upon approval of the request by the patient.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIGS. 7-10 illustrate an example database that may be maintained at the database system at various states in the process flow of FIGS. 2 and 4.

FIG. 11 illustrates an example of access permissions that may be specified by an access request.

DETAILED DESCRIPTION

Figure 1:
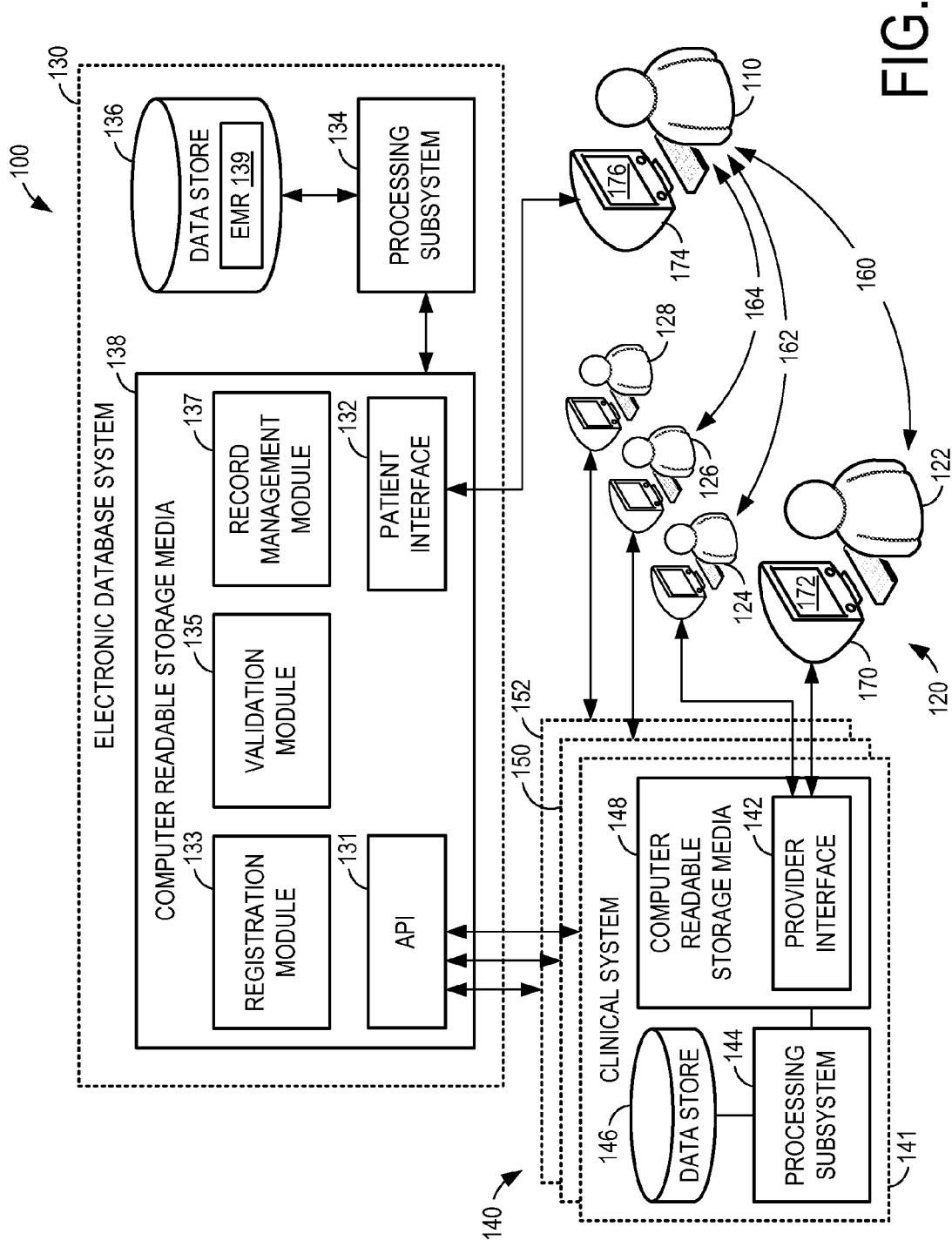
FIG. 1 illustrates an example electronic medical record management system.

FIG. 1 illustrates an electronic medical record management system 100 that facilitates the storage and sharing of electronic medical records between patients and healthcare providers. As a non-limiting example, a patient 110 may access an electronic medical record 139 of the patient stored at a database system 130 via a patient interface 132. Healthcare providers 120, including healthcare provider 122, healthcare provider 124, healthcare provider 126, and healthcare provider 128 may access electronic medical records stored at database system 130 via one or more of clinical systems 140. Clinical systems 140 may serve as intermediaries between healthcare providers 120 and database system 130. For example, healthcare provider 122 may access electronic medical record 139 of patient 110 stored at database system 130 via a provider interface 142 of a clinical system 141.

Patient 110 may refer generally to a consumer of healthcare services. As one example, patient 110 may refer to a person that physically receives healthcare services from one or more healthcare providers. For example, a patient 110 may receive healthcare services from healthcare provider 122 as indicated by interaction 160. Patient 110 may receive healthcare services from other healthcare providers, including healthcare provider 124 and healthcare provider 126 as indicated by interactions 162 and 164, respectively. Patient 110 may also refer to a person that is authorized to act on behalf of the person or animal (in the case of veterinary services) that physically receives the healthcare services from one or more of the healthcare providers. As such, the term "patient" may refer to either the person that physically receives the healthcare services or the person that is authorized to act on behalf of the person or animal that physically receives the healthcare services from the healthcare provider.

Healthcare providers 120 may refer generally to providers of healthcare services. As one example, healthcare providers may refer to persons such as physicians, pharmacists, dentists, ophthalmologists, laboratory technicians, veterinarians, etc. that physically provide healthcare services to patients. Healthcare providers may also refer to other entities that use information stored in a patient's electronic medical record. As further non-limiting examples, fitness clubs, athletic organizations, dieting organizations, or other entities may be referred to as a healthcare provider. Healthcare providers may also refer to persons that are authorized to act on behalf of persons who physically provide the healthcare services to patients. For example, a healthcare provider may also refer to office staff, nursing assistants, pharmacy assistants, veterinary assistants, or other suitable third parties that are authorized to act on behalf of the physicians, pharmacists, dentists, ophthalmologists, laboratory technicians, veterinarians, etc. As such, healthcare providers may refer to any suitable entity having legitimate reason to access electronic medical records of a patient, including health insurance providers, medical researchers, and government agencies.

In some embodiments, database system 130 may utilize a registration process for clinical systems 140 and healthcare providers 120 before permitting these clinical systems and healthcare providers to access the electronic medical records. Referring to FIG. 1, clinical systems 140 may each serve one or more of healthcare providers 120. For example, clinical system 141 may serve healthcare provider 122 and healthcare provider 124, while clinical system 150 and clinical system 152 serve healthcare provider 126 and healthcare provider 128, respectively. In some examples, healthcare provider 122 and healthcare provider 124 may be members of separate healthcare practices, while in other examples, healthcare provider 122 and healthcare provider 124 may be members of the same healthcare practice. In still other examples, a clinical system may serve only a single healthcare provider, whereby the electronic database system may utilize the master-application-identification-code for identifying the healthcare provider.

Before these healthcare providers may access electronic medical records stored at database system 130, clinical systems 140 (e.g. a party that is responsible for the operation and/or maintenance of the clinical system) may first register for a master-application-identification-code, which permits the clinical systems to subsequently obtain child-application-identification-codes on behalf of their respective healthcare providers.

In some embodiments, the party that is responsible for the electronic database system may provide a master-application-identification-code to the party that is responsible for the clinical system, which may be used to request child-application-identification codes on behalf of healthcare providers. It should be appreciated that the clinical system may refer to an online service in some examples, where the healthcare providers may register for the online service. In other examples, the clinical system may refer to a product that is installed at or integrated with a healthcare practice system of a healthcare provider. In either case, the master-application-identification-code may be provided to the party that is responsible for the clinical system for use at their discretion to request that child-application-identification-codes be generated on behalf of participating healthcare providers. Although FIGS. 2 and 3 will be described in the context of a clinical system requesting a master-application-identification-code, it should be appreciated that the master-application-identification-code need not be assigned to a particular clinical system in some examples, but rather to the party that is responsible for the clinical system. The process flows of FIGS. 2 and 3 will be described with reference to healthcare provider 122 and clinical system 141. However, it should be appreciated that the process flows described herein may be applied to other healthcare providers and clinical systems.

Figure 2:
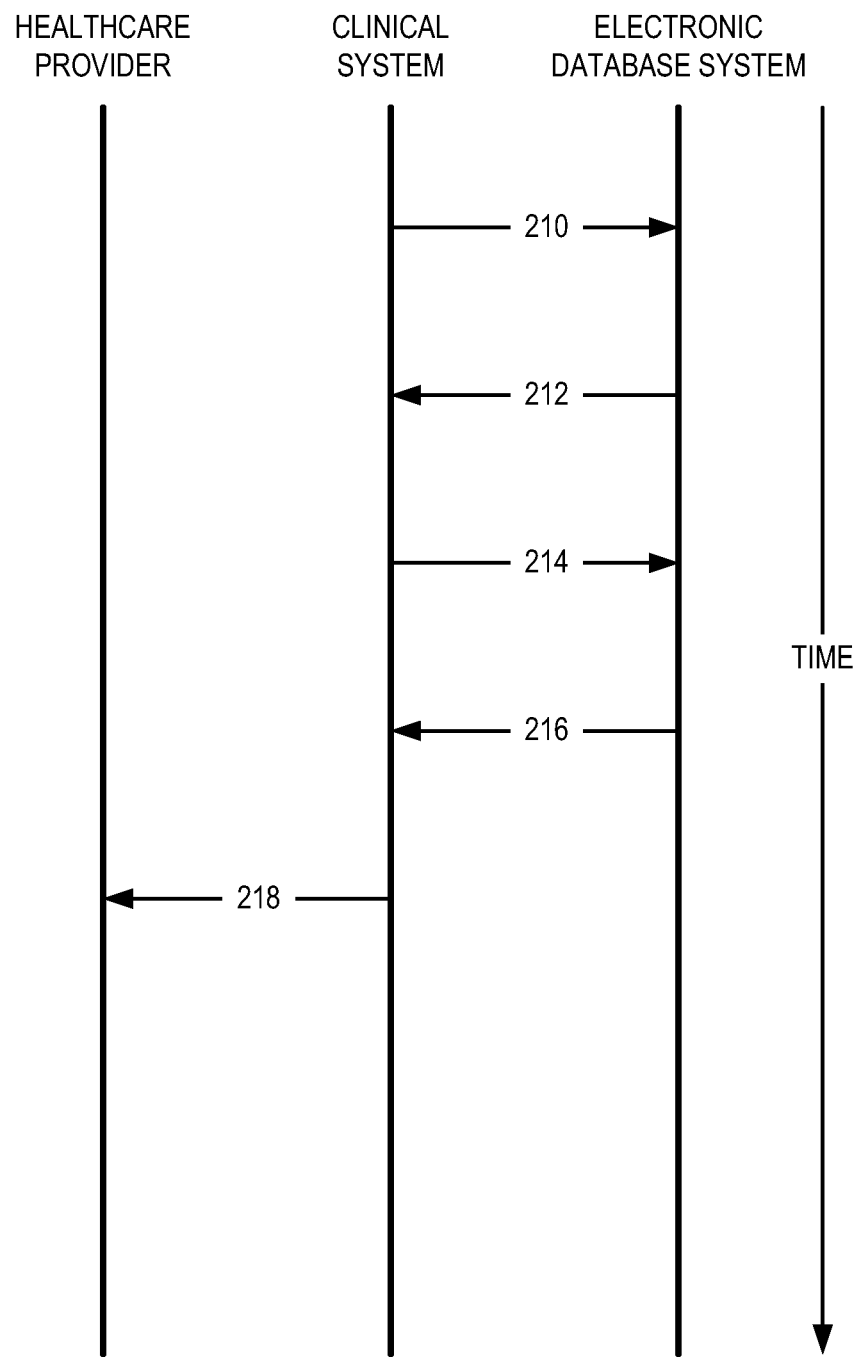
FIG. 2 illustrates an example process flow for registering a clinical system and a healthcare provider with a database system.
Figure 3:
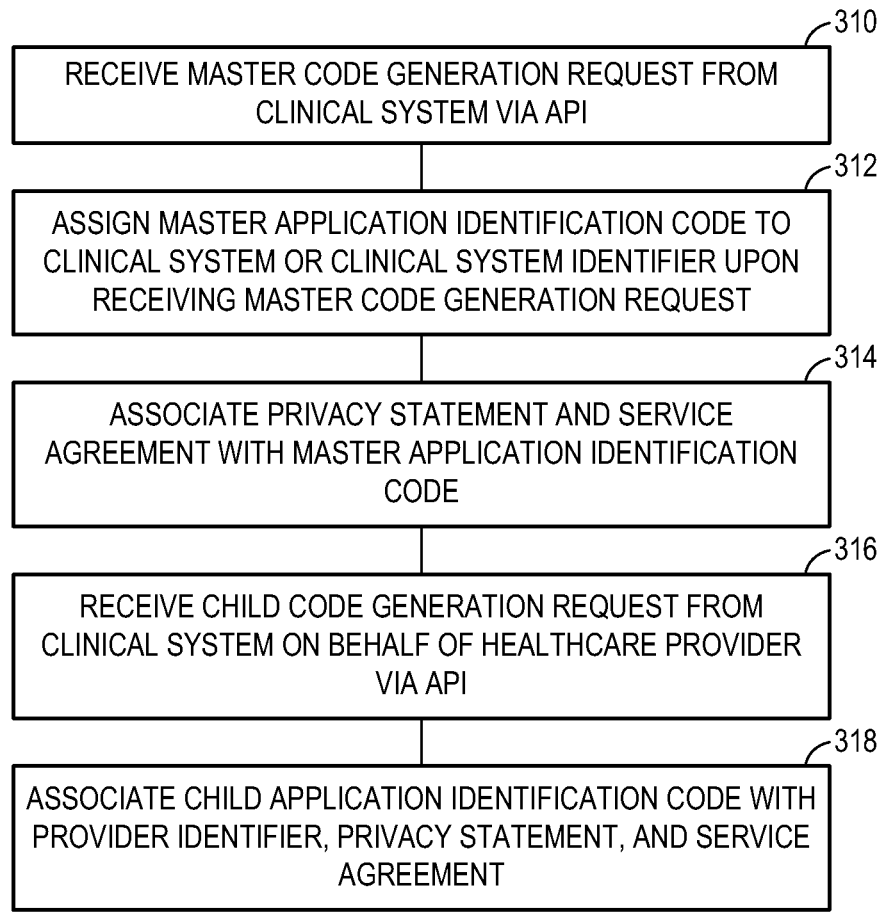
FIG. 3 illustrates the process flow of FIG. 2 from the perspective of the database system.

Beginning at 210 and 310 of FIGS. 2 and 3, a master-code-generation-request may be submitted to database system 130 by clinical system 141 via API 131 (application programming interface). Computer readable storage media 138 may comprise instructions executable by processing subsystem 134 to expose API 131 to clinical systems 140. Computer readable storage media 138 may further comprise instructions executable by processing subsystem 134 to provide a registration module 133. The master-code-generation-request may be received at the database system by the registration module.

In other embodiments, a master-application-identification-code may be requested without submitting a master-code-generation-request via the API. In other words, the party that is responsible for the clinical system may obtain a master-application-identification-code by other suitable approaches without requiring that the clinical system submit an electronic request via the API. For example, the party that is responsible for the electronic database system may provide a master-application-identification-code to the party that is responsible for the clinical system for use by the clinical system for requesting child-application-identification-codes on behalf of the healthcare providers.

The master-code-generation-request may specify a variety of parameters, including one or more of the following: a clinical system identifier identifying the clinical system that submitted the master-code-generation-request, a privacy statement to be associated with the clinical system and its respective healthcare providers, and a service agreement to be associated with the clinical system and its healthcare providers. The registration module may store these parameters at data store 136.

In some embodiments, the clinical system identifier may include one or more of a name, a logo, and a description of the clinical system that has submitted the master-code-generation-request. In other embodiments, the clinical system identifier may include a unique identification code. It should be appreciated that the clinical system identifier may include any suitable identifying information as prescribed by the database system.

The privacy statement may refer generally to any suitable privacy policy information in machine and/or human readable form. The privacy statement may specify how patient information, including medical information of the patient, may be used by the clinical system and the various healthcare providers who are served by the clinical system.

The service agreement may specify terms of use that the patient agrees to when granting the clinical system access to the electronic medical record stored at the database system. In some embodiments, the master-code-generation-request may specify a reference or navigation element (e.g., hyperlink) that may be used to access or retrieve the privacy statement and service agreement. The privacy statement and/or service agreement may be presented to the patient in a manner that enables the patient to decide whether to consent to granting access to a particular healthcare provider or clinical system as will be described with reference to the process flow of FIG. 4.

The registration module may be configured to generate a master-application-identification-code for the clinical system upon receiving the master-code-generation-request. In some embodiments, the master-application-identification-code may include a unique identifier that the clinical system may use to identify itself when interacting with the database system. At 312 of FIG. 3, the registration module may assign the master-application-identification-code to the clinical system upon receiving the master-code-generation-request. For example, the registration module may be configured to store the master-application-identification-code at data store 136 in association with the clinical system identifier. At 314 of FIG. 3, the registration module may associate the privacy statement and the service agreement with the master-application-identification-code. For example, the registration module may be configured to store the privacy statement and the service agreement at data store 136 in association with the master-application-identification-code. It should be appreciated that the privacy statement and service agreement may be represented at the database system as reference or navigation elements to respective privacy statement documents and service agreement documents residing at a remote location (e.g., at data store 146 of clinical system 141). At 212 of FIG. 2, the registration module may return the master-application-identification-code to the clinical system upon receiving the master-code-generation-request from the clinical system.

It should be appreciated that the clinical systems described herein may communicate with the database system via any suitable communication network, including one or more wide area networks and local area networks. These clinical systems may communicate with the database system via symmetric or asymmetric cryptography. As a non-limiting example, data exchanged between clinical system 141 and database system 130 via API 131 may be encrypted through public/private key pairs. For example, database system 130 may provide a digital certificate to the clinical system upon assigning the master-application-identification-code to the clinical system. The digital certificate may include a public key that may be used by the clinical system to encrypt data that may be decrypted by the database system. It should be appreciated that other suitable encryption standards may be used where appropriate.

At 214 and 316 of FIGS. 2 and 3, database system may receive a child-code-generation-request from the clinical system on behalf of healthcare provider 122. The child-code-generation-request may be received by the registration module via API 131. In some embodiments, the child-code-generation-request may specify the master-application-identification-code assigned to the clinical system that submitted the child-code-generation-request to the database system. The child-code-generation-request may further specify a provider identifier identifying the healthcare provider on whose behalf the child-application-identification-code was submitted. In some embodiments, the provider identifier may include one or more of a name, a logo, and a description of the healthcare provider. In some embodiments, the provider identifier may include a unique identification code.

The registration module may generate a child-application-identification-code upon receiving the child-code-generation-request. At 318 of FIG. 3, the registration module may associate the child-application-identification-code with the provider identifier specified by the child-code-generation-request. The registration module may further associate the child-application-identification-code with the privacy statement and the service agreement that were previously associated with the master-application-identification-code at 314 of FIG. 3. These parameters and their respective associations may be stored at data store 136.

At 216 of FIG. 2, the registration module may return the child-application-identification-code to the clinical system that submitted the child-code-generation-request as indicated by the master-application-identification-code. In some embodiments, the registration module may return the child-application-identification-code to the clinical system via the API, along with the provider identifier, so that the clinical system may associate the child-application-identification-code with the appropriate healthcare provider. At 218, the clinical system may optionally forward the child-application-identification-code to the healthcare provider indicated by the provider identifier. Referring to FIG. 7, the master-application-identification-code (i.e., MASTER_APPLICATION_ID) and the child-application-identification-code (i.e., CHILD_APPLICATION_ID) may be optionally stored in data store 146 in association with the provider identifier (i.e., PROVIDER_ID).

In some embodiments, the healthcare provider assigned to the child-application-identification-code may utilize the same digital certificate as the clinical system assigned to the master-application-identification-code that was responsible for submitting the child-code-generation-request. In this way, healthcare providers may use the same public key to communicate with the database system as the clinical system which serves as the intermediary between the database system and the healthcare provider.

The database system may create other child application codes for other healthcare providers served by clinical system 141, including healthcare provider 124. Further, the process flows of FIGS. 2 and 3 may be repeated in order to create respective master-application-identification-codes for clinical system 150 and clinical system 152. Further still, the process flows of FIGS. 2 and 3 may be repeated in order to create respective child-application-identification-codes for healthcare provider 124, 126, and 128.

In this way, the database system may generate master-application-identification-codes for clinical systems that submit master-code-generation-requests. The database system may further generate child-application-identification-codes for clinical systems acting on behalf of healthcare providers after they first obtain a master-application-identification-code. Where the clinical system serves a single healthcare provider or a unified group of healthcare providers acting in concert, the child-application-identification-code may be the same as the master-application-identification-code. Alternatively, a child-application-identification-code may not be assigned, whereby the single healthcare provider or unified group of healthcare providers may utilize the master-application-identification-code of the clinical system when interacting with the database system.

Referring again to FIG. 1, interaction 160 is depicted schematically between patient 110 and healthcare provider 122. As one example, interaction 160 may represent healthcare services being provided to patient 110 by healthcare provider 122. For example, the patient may physically visit the offices of the healthcare provider to receive treatment from the healthcare provider. While in other examples, the patient may remotely receive treatment or monitoring from the healthcare provider via a communication network such as the Internet or telephone. Regardless of the particular manner in which the healthcare provider provides healthcare services to the patient, interaction 160 represents a relationship between the healthcare provider and patient as respective provider and consumer of healthcare services.

Patient 110 may also receive healthcare services from other healthcare providers as indicated by interaction 162 and interaction 164. These other healthcare providers may similarly access electronic medical record 139 of patient 110 stored at database system 130 via their respective clinical systems. Clinical systems 140, including clinical system 141, may refer to one or more of an electronic medical record system, a practice management system, an online service, or other suitable intermediary that facilitates the sharing, storage, and management of patient medical information between healthcare providers 120 and database system 130.

As a consequence of interaction 160, healthcare provider 122 may request permission from patient 110 to access electronic medical record 139 at data store 136 of database system 130. For example, the healthcare provider may request permission to perform various actions with respect to medical information of medical record 139, including reading medical information from the electronic medical record or writing medical information to the electronic medical record.

Figure 4:
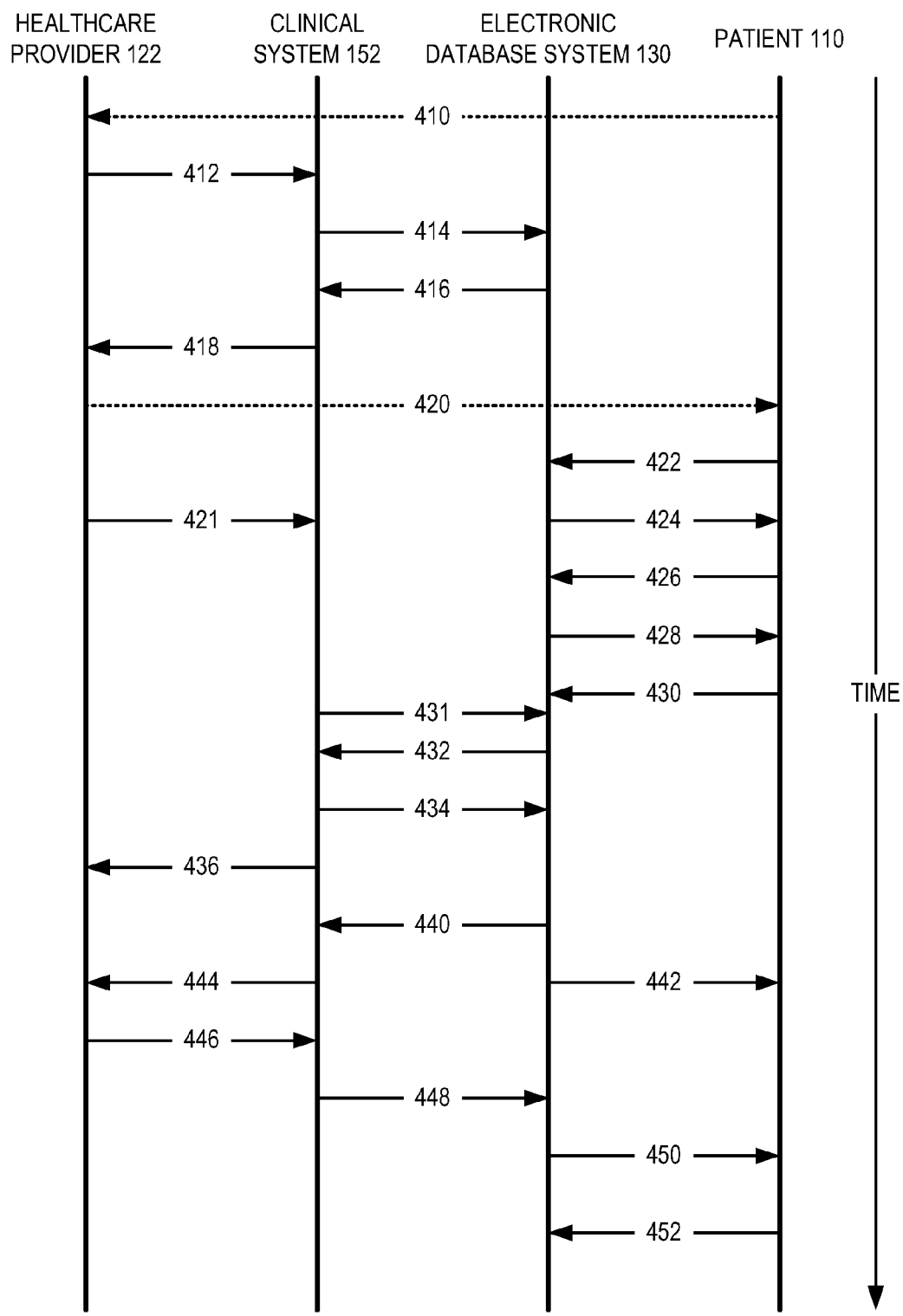
FIG. 4 illustrates an example process flow for obtaining consent from a patient to access an electronic medical record of the patient stored at the database system.
Figure 5:
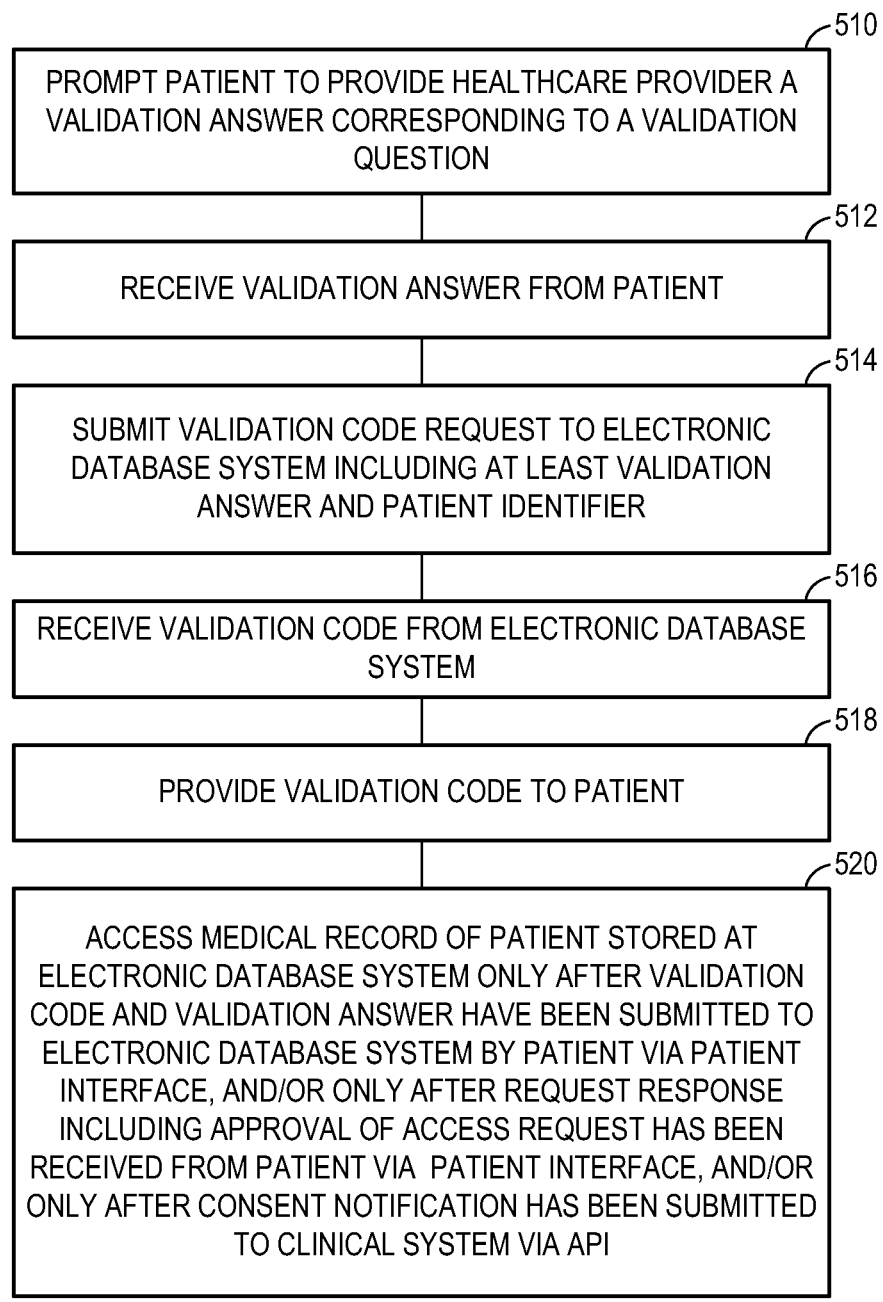
FIG. 5 illustrates the process flow of FIG. 4 from the perspective of a healthcare provider.
Figure 6:
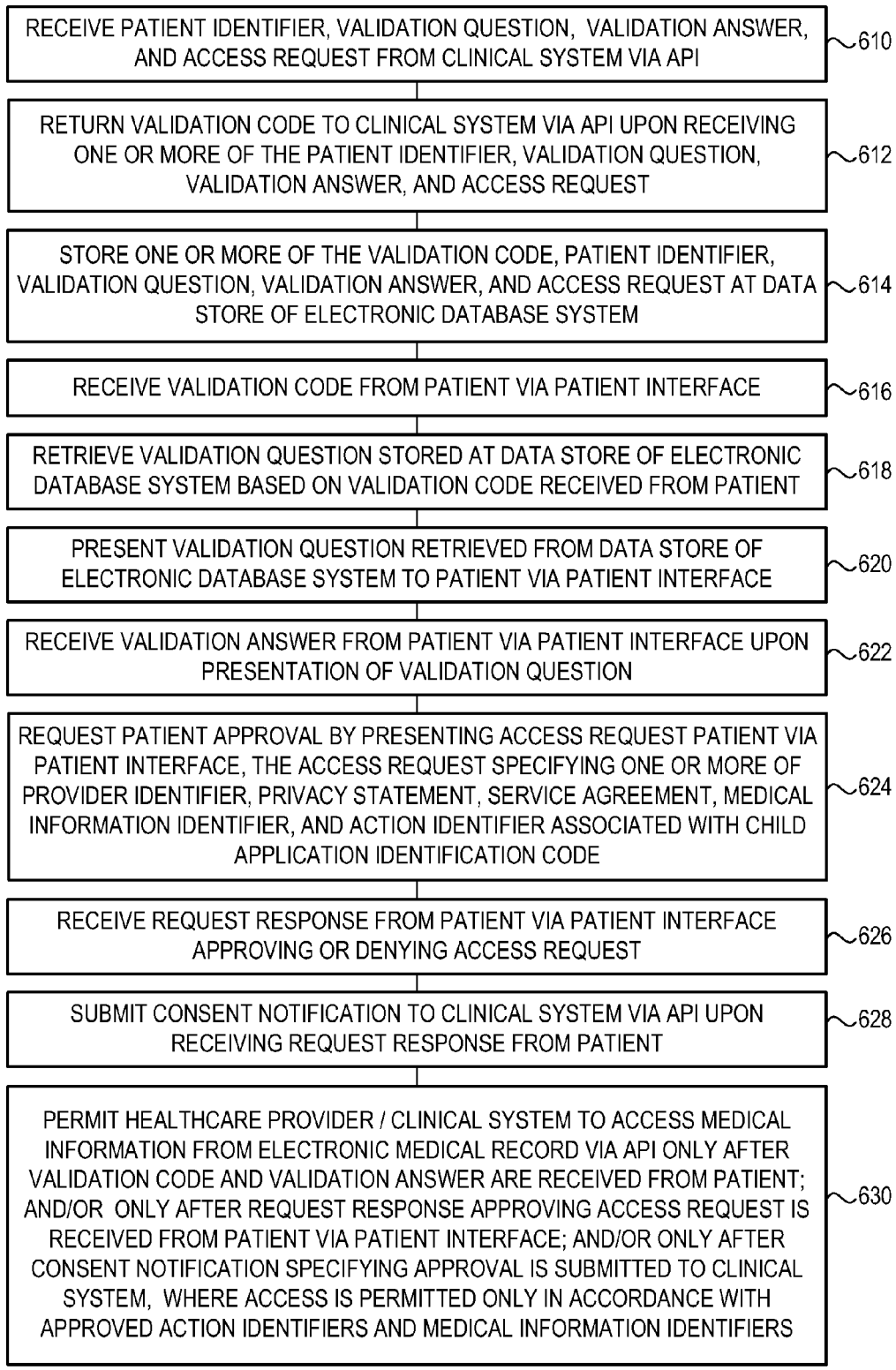
FIG. 6 illustrates the process flow of FIG. 4 from the perspective of the database system.

An example approach for obtaining consent from the patient to access the electronic medical record of the patient stored at the database system is described with reference to the process flows of FIGS. 4-6. FIG. 4 illustrates a process flow depicting how healthcare provider 122 may obtain consent from patient 110 before accessing medical record 139. FIG. 5 illustrates the process flow of FIG. 4 from the perspective of the healthcare provider, while FIG. 6 illustrates the process flow of FIG. 4 from the perspective of the database system.

Referring initially to FIGS. 4 and 5, the healthcare provider may request permission from the patient to access the patient's medical record by prompting the patient to exchange a shared secret with the healthcare provider. If the patient provisionally consents to this request, then the healthcare provider and the patient may exchange the shared secret. This shared secret may be later used by the patient to formally consent to the request of the healthcare provider. For example, at 510 of FIG. 5, the healthcare provider may prompt the patient by providing the patient with a validation question, to which the patient may respond with a validation answer corresponding to the validation question.

In some embodiments, the validation question may prompt the patient to provide a validation answer to the healthcare provider that is both factual and personal to the patient. For example, the validation question may inquire as to a maiden name of the patient's mother, the patient's city of birth, or a name of the patient's first pet, among other suitable questions. As indicated at 410 of FIG. 4, the validation answer may be provided to the healthcare provider by the patient, where the healthcare provider may receive the validation answer from the patient at 512 of FIG. 5.

The healthcare provider, upon receiving the validation answer from the patient at 512 of FIG. 5, may submit a validation request to the database system at 514 of FIG. 5. In some embodiments, the healthcare provider may submit the validation request to the database system via a clinical system, such as clinical system 141 as indicated at 412 of FIG. 4. As one example, healthcare provider 122 may submit the validation request to clinical system 141 via provider interface 142.

In some embodiments, the provider interface may be exposed to healthcare provider 122 via a computing device 170. Provider interface 142 may include a graphical user interface 172 that may be presented to the healthcare provider via a display of computing device 170. Computing device 170 may be communicatively coupled with clinical system 141 via one or more of a wide area network (WAN) (e.g., the Internet) and a local area network (LAN).

Clinical system 141 may further include a data store 146 configured to store medical information that may be accessed by healthcare provider 122. In some embodiments, data store 146 may be configured to store a local version of medical information that the healthcare provider may access without communicating with database system 130. Clinical system 141 may further include a computer readable storage media 148 comprising instructions executable by processing subsystem 144. As one example, the instructions executable by processing subsystem 144 may expose provider interface 142 to one or more of healthcare providers 120.

The validation request may specify one or more of the following parameters: the child-application-identification-code associated with the healthcare provider, the validation question, the validation answer, a patient identifier identifying the patient, a provider identifier identifying the healthcare provider, and an access request. In some embodiments, the validation request may not specify the validation question. For example, the validation question may be generated by the clinical system or the database system on behalf of the healthcare provider.

The patient identifier specified by the validation request may include any suitable form of identification for the patient. For example, the patient identifier may include a unique identification code of the patient that is assigned to the patient by a healthcare provider or clinical system to refer to the patient. This unique identification code may not include personally identifiable information of the patient in some examples. As another example, the patient identifier may include the patient's name. In some embodiments, the clinical system may generate the patient identifier on behalf of the healthcare provider.

The access request which may be specified by the validation code request may further specify a medical information identifier and an action identifier. The medical information identifier identifies medical information to be accessed by the healthcare provider via the clinical system upon approval of the access request by the patient. The action identifier identifies one or more actions to be performed by the healthcare provider with respect to the medical information identified by the medical information identifier. For example, the action identifier may identify whether the healthcare provider may read the corresponding medical information from the electronic medical record or write the corresponding medical information to the electronic medical record.

Furthermore, the action identifier may further include or identify a reason or rationale for why the healthcare provider or clinical system is requesting access of the medical record of the patient. The reason or rationale identified by access request may be presented to the patient when the patient is prompted by the electronic database system to approve or deny the access request. In this way, the patient may make a more educated decision on whether to approve or deny a particular access request.

FIG. 11 illustrates example access permissions that may be specified by an access request. Each access permission may include a corresponding medical information identifier and an action identifier. A first set of access permissions specified by access request 1110 includes a medical information identifier "medications" and two corresponding action identifiers "read" and "write". Upon approval of the access permissions specified by access request 1110, the healthcare provider that submitted the access request may access the medical information identified by the medical information identifier in accordance with the action identifiers. For example, upon approval of access request 1110, the healthcare provider may be permitted to read medical information identified by the medical information identifier from the electronic medical record of the patient and may be permitted to write medical information identified by the medical information identifier to the electronic medical record of the patient.

A second access request is shown at 1120 including a medical information identifier "immunizations" and a corresponding action identifier "read". A third access request is shown at 1130, which may include a plurality of medical information identifiers and corresponding action identifiers for each. As a non-limiting example, access request 1130 may correspond to a request by the healthcare provider to access all of the medical information of the electronic medical record. In some embodiments, each of the access permissions specified by the medical information identifier and corresponding action identifier may be approved or denied by the patient on an individual basis, while in other embodiments the patient may approve or deny all of the access permissions as a group. In some embodiments, the access request may be generated on behalf of the healthcare provider by the clinical system. In these embodiments, the validation code request may not include the access request or the access request may be appended to the validation code request after the healthcare provider has submitted the validation code request to the clinical system.

At 414 of FIG. 4, the clinical system may submit or forward the validation code request to the database system via API 131. At 610 of FIG. 6, the database system may receive the validation code request from the clinical system via the API, including one or more of the patient identifier, the validation question, the validation answer, and the access request. In some embodiments, computer readable storage media 138 may comprise instructions executable by processing subsystem 134 to provide a validation module which may receive the validation request. The validation module may be configured to generate a validation code upon receiving the validation code request via the API. As a non-limiting example, the validation code generated by the database system may include a unique alphanumeric code comprising 16 characters. However, it should be appreciated that the validation code may include any suitable number of alphabetic, numeric, and/or other characters. In some embodiments, the validation code may comprise 32 or less characters. In some embodiments, the validation code may not include the letter "O" and the number "0" to reduce confusion between these similarly shaped characters.

Referring to FIG. 8, the validation code (i.e., VALIDATION_CODE) may be stored at the database system in a PENDING_REQUESTS table along with one or more of the validation question (i.e., VALIDATION_QUESTION), the validation answer (i.e., VALIDATION_ANSWER), the child-application-identification-code (i.e., CHILD_APPLICATION_ID) associated with the healthcare provider, and the patient identifier (PATIENT_ID). At 614 of FIG. 6, upon receiving the validation request from the clinical system, the master-application-identification-code (i.e., MASTER_APPLICATION_ID) of the clinical system, the child-application-identification-code (i.e., CHILD_APPLICATION_ID), the provider identifier (i.e., PROVIDER_ID), the access permissions specified by the access request (i.e., REQUESTED_DATA), the privacy statement (PRIVACY_STATEMENT), and the service agreement (i.e., SERVICE_AGREEMENT) may be stored at an APPLICATIONS table. The public key (i.e., PUBLIC_KEY) used to communicate with the clinical system may also be stored at the APPLICATIONS table in association with the child or master-application-identification-code. Note that the master-application-identification-code, the child-application-identification-code, the provider identifier, the public key, the privacy statement, and the service agreement may be stored at the APPLICATIONS table in association with the registration process described with reference to FIGS. 2 and 3. Upon receiving the validation code request, the validation module may set the status indicator (i.e., STATUS) in the PENDING_REQUESTS table to PENDING.

As 416 and 612 of FIGS. 4 and 6, the database system may return the validation code to the clinical system via the API upon receiving validation code request at 414. The clinical system in turn may receive the validation code from the database system via the API upon submission of the validation code request to the database system. In some embodiments, the database system may return the validation code to the clinical system in the form of a validation code response. The validation code response may further specify one or more of the child-application-identification-code associated with the healthcare provider and the patient identifier. In this way, the clinical system may associate the validation code received from the database system with the appropriate healthcare provider and patient. In some embodiments, the validation code received from the database system may be optionally stored in data store 146 of the clinical system.

At 418 of FIG. 4, the clinical system may optionally forward the validation code to the healthcare provider via provider interface 142. As one example, the validation code may be displayed to the healthcare provider via graphical user interface 172 of computing device 170. In some embodiments, the validation code may be presented to the healthcare provider in a hyphen delimited manner. For example, where the validation code comprises 16 characters, the validation code may be displayed in 4 blocks of 4 characters each. A non-limiting example of a validation code may include: Q2W3-E4R6-T6Y7-U9PL. In some embodiments, each of the alphabetic characters of the validation code may be presented to the healthcare provider and patient in an entirely uppercase format. In this way, the validation code may be presented to the healthcare provider and eventually to the patient, in a manner that improves the readability of the validation code. At 516 of FIG. 5, the healthcare provider may receive the validation code from the database system via the clinical system upon submission of the validation request, including at least the validation answer and the patient identifier to the database system.

At 420 and 518 of FIGS. 4 and 5, the validation code may be provided to the patient. In some embodiments, the healthcare provider may provide the validation code to the patient before conclusion of interaction 160. For example, the healthcare provider may provide the patient with instruction materials that include the validation code. The instruction materials may further include instructions for the patient to submit the validation code to the database system. For example, the instruction materials may include a uniform resource locator (URL) indicating a web page where the patient is to submit the validation code to the database system.

As a non-limiting example, patient 110 may submit the validation code and the validation answer to the database system via patient interface 132. For example, patient interface 132 may be exposed to patient 110 by a GUI 176 displayed via a computing device 174. As a non-limiting example, patient interface 132 may be exposed to patient 110 via a web browser that may be displayed to the patient at GUI 176. As such, a web page indicated by the URL included with the instruction materials may be presented to the patient via computing device 174. In some embodiments, these instruction materials may not include the validation answer so as to reduce the likelihood that third parties discover or deduce the validation answer from the instruction materials. Since the validation answer may be personal to the patient, the patient may be better able to later recall the validation answer when prompted with the validation question.

In some embodiments, the instruction materials, including the validation code, may be physically handed to the patient before the patient leaves the office of the healthcare provider. In other embodiments, the validation code may be transmitted to the patient by the healthcare provider. For example, the instruction materials, including the validation code, may be mailed to the patient or to the patient's residence. As another example, the healthcare provider may transmit the validation code to the patient by emailing the instruction materials to the patient or to an email address of the patient. In still other embodiments, the clinical system or the database system may transmit the validation code to the patient by mailing or emailing on behalf of the healthcare provider. In these embodiments, the validation code may not be presented to the healthcare provider. As such, it should be appreciated that the patient may receive the validation code in a number of ways, while retaining a suitable level of confidentiality.

Meanwhile, at 421 of FIG. 4, the healthcare provider may optionally update medical information of the patient stored locally at the clinical system. For example, the healthcare provider may periodically submit medical information to the clinical system for storage at data store 146. It should be appreciated that the medical information of the patient stored at data store 146 may differ at times from the electronic medical record of the patient stored at data store 136 of the database system. As a non-limiting example, the medical information stored at data store 146 may include more, less, or different medical information than the electronic medical record stored at data store 136 for the same patient. The medical information of the patient stored at data store 146 may be later written to the medical record stored at 136 upon approval of the access request by the patient.

Regardless of the particular manner by which the patient receives the validation code, the patient may subsequently submit the validation code to the database system at 422 of FIG. 4. As one example, the database system may prompt the patient to submit the validation code to the database system via the patient interface. In some embodiments, the patient interface may include a webpage. However, it should be understood that the terms web page, web browser, and web server are used to refer to any network information, network user interface, and network server, and should not be narrowly construed as corresponding only to the World Wide Web of the Internet. At 616 of FIG. 6, the validation code may be received from the patient by the database system via the patient interface. For example, at 618 of FIG. 6, validation module 135 may receive the validation code and may retrieve the validation question stored at data store 136 of the database system based on the validation code received from the patient.

At 424 and 620 of FIGS. 4 and 6, the validation question that is retrieved from the data store may be presented to the patient via the patient interface. For example, the validation module may cause the validation question to be displayed to the patient via the patient interface, thereby prompting the patient to submit the validation answer to the validation question. The validation question may be displayed to the patient via GUI 176 of computing device 174, for example. At 426 and 622 of FIGS. 4 and 6, the validation answer may be received from the patient via the patient interface upon presentation of the validation question to the patient. The validation module may compare the validation answer received from the patient via the patient interface to the validation answer that was previously received from the clinical system and stored at the data store.

If the validation answer received from the patient matches the validation answer stored at data store 136, the database system may present the patient with the access request via the patient interface as indicated at 428 and 624 of FIGS. 4 and 6. Alternatively, if the validation answer received from the patient does not match the validation answer stored at the data store, the database system may again present the validation question to the patient via the patient interface, thereby prompting the patient to re-enter the validation answer. In some embodiments, the patient may have a certain number of opportunities or attempts to correctly enter the validation answer. For example, the clinical system may provide the patient with three attempts to correctly enter the validation answer. If the patient does not correctly enter the validation answer within a prescribed number of attempts, the patient may not approve access to the medical record stored at the electronic database system for the healthcare provider until receiving and submitting a new subsequent validation code and corresponding validation answer.

In some embodiments, delimiting characters of the validation code may be ignored when evaluating the validation code submitted by the patient. Further, in some embodiments, the validation code may be evaluated by the validation module by comparing the validation code submitted by the patient at 422 to the validation code stored at the data store in a case insensitive manner, while also ignoring hyphens or other delimiters that may be submitted by the patient along with the validation code characters.

Upon receiving the validation answer from the patient that matches the validation answer stored at data store 136, the validation module may retrieve the access request from data store 136. For example, the validation module may retrieve one or more of the provider identifier, privacy statement, service agreement, medical information identifiers, and action identifiers associated with the child-application-identification-code specified by the access request.

At 428 and 624 of FIGS. 4 and 6, the validation module may request patient approval of the access request by presenting the access request to the patient. As a non-limiting example, the validation module may present one or more of the provider identifier, privacy statement, service agreement, medical information identifiers, and action identifiers to the patient via the patient interface. In some embodiments, the validation module may cause the provider identifier to be displayed to the patient via GUI 176, along with one or more of the privacy statement, service agreement, medical information identifiers, and action identifiers. Presentation of the provider identifier with the privacy statement, service agreement, and access permissions may enable the patient to make a trust decision as to whether the access request should be approved, denied, or approved in part by the patient. At 430 of FIG. 4, the patient may respond to the access request presented at 428 by submitting a request response to the database system via the patient interface.

At 626 of FIG. 6, the database system may receive the request response from the patient via the patient interface, whereby the request response indicates approval or denial of some or all of the access permissions specified by the access request. In some embodiments, the validation module may store an approved or denied status indicator at data store 136 for each access permission specified by the various medical information identifiers and action identifiers. Note that in some embodiments, the patient may approve or deny the entire access request, while in other embodiments the patient may approve or deny portions of the access request. For example, referring again to FIG. 11, an approved or denied indicator may be stored in each relevant field of the various access permissions specified by the access request.

Referring to FIG. 9, the validation module may update the status indicator to ACCEPTED at the PENDING_REQUESTS table upon receiving a request response that includes an approval of the access request. The validation module may be further configured to generate a person identification code (PERSON_ID) and a record identification code (RECORD_ID) that may be used to identify the person and record associated with the patient's approval of the access request upon receiving the request response from the patient via the patient interface. The validation module, upon receiving a request response approving the access request, may be further configured to store the child-application-identification-code associated with the healthcare provider at an APPLICATION_AUTHORIZATIONS table along with the PERSON_ID and the RECORD_ID. An AUTHORIZATION_RULES field may be populated with status indicators either approving or denying each of the access permissions specified by the access request (i.e., REQUESTED_DATA). For example, the access request depicted at 1110 of FIG. 11 includes a medical information indicator MEDICATIONS and approved action indicators READ and WRITE. Where both read and write actions have been approved by the patient, the AUTHORIZATION_RULES may be populated with status indicators that represent the approval of the access permissions specified by the access request. The record management module may interpret the AUTHORIZATION_RULES to permit the healthcare provider associated with the child-application-identification-code stored in the APPLICATION_AUTHORIZATIONS table to access the electronic medical record of the patient in accordance with the approved medical information indicators and action indicators.

In some embodiments, the clinical system may periodically poll the database system for new patient authorizations. As indicated at 431 of FIG. 4, the clinical system may periodically submit to the database system via the API, a request for new patient authorizations along with one or more of the child-application-identification-code of the healthcare provider and the master-application-identification-code of the clinical system. The clinical system may additionally submit a last poll time to the database system along with the application identification code and the request for new patient authorizations.

The database system, upon receiving the request for new patient authorizations may return patient authorizations that have occurred since the last poll time. As a non-limiting example, at 432 of FIG. 4 and 628 of FIG. 6, the electronic database system may be configured to submit or return a consent notification to the clinical system via the API upon receiving the request response from the patient, or upon receiving the request for new patient authorizations from the clinical system. As a non-limiting example, the consent notification may specify one or more of the master-application-identification-code assigned to the clinical system, the child-application-identification-code assigned to the healthcare provider, the patient identifier, the person identification code, and the record identification code. It should be appreciated that the database system may communicate other suitable parameters to the clinical system, including the approval and denial of the various access permissions indicated by the request response received from the patient at 430 of FIG. 4.

In some embodiments, the clinical system may provide a URL address to the electronic database system where the electronic database system may submit the consent notification. The clinical system and/or the healthcare provider may in turn receive the consent notification via the URL address that was provided to electronic database system upon approval of the access request by the patient.

The clinical system may store one or more of the parameters specified by the consent notification at data store 146. For example, referring also to FIG. 10, the person identification code (i.e., PERSON_ID) and the record identification code (i.e., RECORD_ID) may be stored at the PATIENTS table of the clinical system in association with the PAITIENT_ID. The validation module may also update the status indicator (i.e., STATUS) at the PENDING_REQUESTS table upon submission of the consent notification to the clinical system via the API.

At 520 of FIG. 5 and 630 of FIG. 6, the database system may permit the healthcare provider and/or clinical system to access the electronic medical record of the patient stored at data store 136 in accordance with the request response received from the patient at 430 (i.e., the approved access permissions). In some embodiments, computer readable storage media 138 may comprise instructions executable by the processing subsystem to provide a record management module 137. Record management module 137 may be configured to manage access to the electronic medical records stored at data store 136 by healthcare providers 120 and clinical systems 140 in accordance with the access request approved by the patient.

As a first example, the record management module of the database system may be configured to permit the healthcare provider and/or clinical system to access the electronic medical record of the patient stored at the database system only after the validation code and the validation answer have been submitted to the database system by the patient via the patient interface. For example, at 434 of FIG. 4, the healthcare provider and/or the clinical system may access the medical record of the patient by submitting medical information to the database system to cause the electronic medical record to be updated (i.e., written) with the medical information only after the validation code and the validation answer have been submitted to the database system by the patient via the patient interface. The medical information submitted at 434 of FIG. 4 may include medical information submitted to the clinical system at 421 by the healthcare provider. At 440 of FIG. 4, the healthcare provider and/or clinical system may access the medical record of the patient by receiving (i.e., reading) medical information from the medical record only after the validation code and the validation answer have been submitted to the database system by the patient via the patient interface. The medical information received by the clinical system at 440 may be optionally stored at data store 146 where it may be accessed by the healthcare provider via the provider interface. In other examples, the medical information received by the clinical system at 440 may be optionally forwarded to the healthcare provider via the provider interface as indicated at 444 of FIG. 4.

As another example, the record management module of the database system may be configured to permit the healthcare provider and/or clinical system to access the electronic medical record of the patient stored at the database system only after the request response approving the access request has been received from the patient via the patient interface. As a non-limiting example, the record management module may be configured to check the PENDING_REQUESTS table for the presence of one or more of the ACCEPTED or COMPLETE status indicators before permitting the clinical system or healthcare provider to access the electronic medical record. For example, at 434 of FIG. 4, the healthcare provider and/or the clinical system may access the medical record of the patient by submitting medical information to the database system to cause the electronic medical record to be updated with the medical information only after the request response approving the access request has been received from the patient via the patient interface. For example, at 440 of FIG. 4, the healthcare provider and/or clinical system may access the medical record of the patient by receiving medical information from the medical record only after the request response has been received by the patient via the patient interface.

As yet another example, the record management module of the database system may be configured to permit the healthcare provider and/or clinical system to access the electronic medical record of the patient stored at the database system only after the consent notification specifying the approval of the access request by the patient is submitted to the clinical system by the database system via the API. As a non-limiting example, the record management module may be configured to check the PENDING_REQUESTS table for the presence of the COMPLETE status indicator before permitting the clinical system or healthcare provider to access the electronic medical record. For example, at 434 of FIG. 4, the healthcare provider and/or the clinical system may access the medical record of the patient by submitting medical information to the database system to cause the electronic medical record to be updated with the medical information only after consent notification specifying the approval of the access request is submitted to the clinical system via the API. For example, at 440 of FIG. 4, the healthcare provider and/or clinical system may access the medical record of the patient by receiving medical information from the medical record only after the consent notification specifying the approval of the access request has been submitted to the clinical system via the API.

In each of the above examples, the healthcare provider and/or the clinical system may be permitted to access only the medical information identified by the approved medical information identifiers in accordance with the approved action identifiers. As indicated at 436 of FIG. 4, the clinical system may optionally forward the consent notification to the healthcare provider upon receiving the consent notification from the database system at 432. As indicated at 442 of FIG. 4, the clinical system may optionally notify the patient when the electronic medical record of the patient is accessed by the healthcare provider or the clinical system. This notification may specify one or more of the provider identifier and the clinical system identifier, as well as the medical information accessed and the action taken with respect to the medical information. This notification may be emailed to the patient or may otherwise be displayed to the patient via GUI 176.

As indicated at 446, 448, 450, and 452 of FIG. 4, the healthcare provider may submit subsequent access requests to amend the access permissions approved by the patient. For example, the healthcare provider may initially submit access request 1110 of FIG. 11 to the database system for approval by the patient and may later submit at 446 of FIG. 4 access request 1130 of FIG. 11. The clinical system may forward the subsequent access request to the database system at 448 of FIG. 4 as previous described. At 450 of FIG. 4, the subsequent access request may be presented to the patient as previously described with reference to 428. At 452 of FIG. 4, the patient may submit a subsequent request response to the database system via the patient interface. The subsequent request response may approve or deny access permissions that were specified by the original access request and may approve or deny access permissions specified by the subsequent access request. The healthcare provider and/or the clinical system may access the electronic medical record of the patient in accordance with the approved access permissions specified by the subsequent request response. Once the patient has initially submitted the validation code and validation answer, the patient may adjust the approved status of the access permissions at any time. In this way, the patient may change or update the approved access permissions without necessarily requiring additional shared secrets to be exchanged between the healthcare provider and the patient.

In some embodiments, the patient may revoke the approved status of some or all of the access permissions at any time via the patient interface, whereby the healthcare provider and/or clinical system may no longer be permitted to access the medical record of the patient stored at the database system. As a non-limiting example, the validation module may be configured to update the AUTHORIZATION_RULES field of the APPLICATION_AUTHORIZATIONS table in accordance with the subsequent request response of the patient.

It will be appreciated that the computing devices described herein may be any suitable computing device configured to execute programs. For example, the computing devices may be a mainframe computer, personal computer, laptop computer, portable data assistant (PDA), computer-enabled wireless telephone, networked computing device, or other suitable computing device, and may be connected to each other via computer networks, such as the Internet. These computing devices typically include a processor and associated volatile and non-volatile computer readable storage media, and are configured to execute programs stored in non-volatile computer readable storage media using portions of volatile computer readable storage media and the processor. It will be appreciated that computer-readable media may be provided having program instructions stored thereon, which upon execution by a computing device, cause the computing device to execute the methods described above and cause operation of the systems described above.

It should be understood that the embodiments herein are illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A method of obtaining consent from a patient for a healthcare provider to access an electronic medical record of the patient stored at a database system, the method comprising:
   prompting, by the healthcare provider, a patient to provide the healthcare provider a validation answer corresponding to a validation question;
   receiving, by the healthcare provider, the validation answer from the patient;
   submitting, via a computing device including a display configured to display a graphical user interface of a first, provider interface, the validation answer and a patient identifier identifying the patient to the database system;
   receiving, by the healthcare provider via the first, provider interface, a validation code from the database system upon submission of the validation answer and the patient identifier to the database system;
   providing the validation code to the patient; and
   accessing the electronic medical record of the patient stored at the database system with permission from the database system only after the validation code and the validation answer have been submitted to the database system by the patient via a second, patient interface that is different from the first, provider interface.

2. The method of claim 1, further comprising, accessing the electronic medical record of the patient at the database system by receiving medical information from the electronic medical record only after the validation code and the validation answer have been submitted to the database system by the patient via the patient interface.

3. The method of claim 1, further comprising, accessing the electronic medical record of the patient at the database system by submitting medical information to the database system to cause the electronic medical record to be updated with the medical information only after the validation code and the validation answer have been submitted to the database system by the patient via the patient interface.

4. The method of claim 1, where the patient interface includes a web page and where the method further comprises:
   providing the patient with a uniform resource locator indicating the web page where the patient is to submit the validation code and the validation answer to the database system.

5. The method of claim 1, where providing the validation code to the patient further includes providing instruction materials to the patient including the validation code; where the instruction materials further include instructions for the patient to submit the validation code to the database system via the patient interface.

6. The method of claim 5, where the instruction materials do not include the validation answer.

7. The method of claim 5, where providing the validation code to the patient further includes mailing the instruction materials to the patient.

8. The method of claim 5, where providing the validation code to the patient further includes emailing the instruction materials to the patient.

9. The method of claim 1, where submitting the validation answer and the patient identifier to the database system via the provider interface includes submitting the validation answer and the patient identifier to a clinical system that exposes the provider interface via the graphical user interface, the clinical system communicating with the database system via an application programming interface.

10. The method of claim 1, where receiving the validation code from the database system includes receiving the validation code via the provider interface.

11. The method of claim 1, further comprising, submitting an access request to the database system via the provider interface, the access request specifying a medical information indicator identifying medical information to be accessed by the healthcare provider from the electronic medical record.

12. A database system, comprising:
a data store configured to store an electronic medical record of a patient;
a processing subsystem configured to execute instructions; and
computer readable storage media comprising instructions executable by the processing subsystem to:
receive from a clinical system via an application programming interface: a patient identifier identifying the patient, a validation question, and a validation answer corresponding to the validation question;
return a validation code to the clinical system via the application programming interface upon receiving the patient identifier, the validation question, and the validation answer;
receive the validation code and the validation answer from the patient via a patient interface that is different from the application programming interface; and
submit medical information from the electronic medical record to the clinical system via the application programming interface only after the validation code and validation answer are received from the patient via the patient interface.

13. The database system of claim 12, where the computer readable storage media further comprise instructions executable by the processing subsystem to:
present the patient with an access request via the patient interface, the access request specifying a medical information identifier identifying the medical information to be submitted to the clinical system via the application programming interface;
receive a request response from the patient via the patient interface upon presentation of the access request to the patient, the request response approving the access request or denying the access request; and
submit the medical information identified by the medical information identifier from the electronic medical record to the clinical system via the application programming interface only after the request response approving the access request has been received from the patient via the patient interface.

14. The database system of claim 13, where the computer readable storage media further comprise instructions executable by the processing subsystem to:
receive the access request from the clinical system via the application programming interface; and
store the access request at the data store before the access request is presented to the patient via the patient interface.

15. The database system of claim 13, where the computer readable storage media further comprise instructions executable by the processing subsystem to:
submit a consent notification to the clinical system via the application programming interface upon receiving the request response from the patient, the consent notification specifying an approval or a denial of the access request by the patient as indicated by the request response.

16. The database system of claim 15, where the computer readable storage media further comprise instructions executable by the processing subsystem to:
submit the medical information identified by the medical information identifier to the clinical system via the application programming interface only after the consent notification specifying the approval of the access request by the patient is submitted to the clinical system via the application programming interface.

17. The database system of claim 13, where the computer readable storage media further comprise instructions executable by the processing subsystem to:
receive the medical information identified by the medical information indicator from the clinical system via the application programming interface; and
update the electronic medical record of the patient at the data store with the medical information received from the clinical system via the application programming interface only after the request response approving the access request is received from the patient via the patient interface.

18. The database system of claim 12, where the computer readable storage media further comprise instructions executable by the processing subsystem to:
present the validation question to the patient via the patient interface after the validation code is received from the patient and before the validation answer is received from the patient, the validation question prompting the patient to submit the validation answer corresponding to the validation question via the patient interface.

19. A method of facilitating access to an electronic medical record of a patient by a healthcare provider via a database system, the method comprising:
receiving a validation code request from a healthcare provider via a computing device including a display configured to display a graphical user interface of a first, provider interface, the validation code request specifying a patient identifier identifying a patient, a validation question, and a validation answer corresponding to the validation question;
submitting a validation code to the healthcare provider upon receiving the validation code request from the healthcare provider;
storing at least the validation code, the validation question, and the validation answer at a data store of the database system;
receiving the validation code from the patient via a second, patient interface that is different from the first, provider interface;
retrieving the validation question stored at the data store of the database system based on the validation code received from the patient;
presenting the validation question retrieved from the data store of the database system to the patient;
receiving the validation answer from the patient via the second, patient interface upon presentation of the validation question to the patient; and
permitting the healthcare provider to access the electronic medical record of the patient stored at the data store of the database system only after the validation code and the validation answer have been received from the patient via the second, patient interface.

20. The method of claim 19, further comprising:
- receiving an access request from the healthcare provider, the access request specifying medical information to be accessed by the healthcare provider from the electronic medical record;
- presenting the patient with the access request, including the medical information requested by the healthcare provider;
- receive a request response from the patient via the patient interface upon presentation of the access request to the patient, the request response approving the access request or denying the access request; and
- permitting the healthcare provider to access the medical information from the electronic medical record only after the request response approving the access request is received from the patient via the patient interface.

* * * * *